(12) United States Patent
Sorkin (10) Patent No.: US 10,071,530 B2
(45) Date of Patent: Sep. 11, 2018

(54) COLLAPSIBLE ELEMENT POCKET FORMER

(71) Applicant: Felix Sorkin, Stafford, TX (US)

(72) Inventor: Felix Sorkin, Stafford, TX (US)

( * ) Notice: Subject to any disclaimer, the term of this patent is extended or adjusted under 35 U.S.C. 154(b) by 0 days.

(21) Appl. No.: 15/815,334

(22) Filed: Nov. 16, 2017

(65) Prior Publication Data
US 2018/0072006 A1  Mar. 15, 2018

Related U.S. Application Data

(62) Division of application No. 15/226,487, filed on Aug. 2, 2016, now Pat. No. 9,827,721.

(60) Provisional application No. 62/200,966, filed on Aug. 4, 2015.

(51) Int. Cl.
| | |
|---|---|
| *B29C 70/54* | (2006.01) |
| *E04C 5/12* | (2006.01) |
| *B28B 7/30* | (2006.01) |
| *B28B 1/14* | (2006.01) |
| *E04C 5/16* | (2006.01) |
| *E04C 5/07* | (2006.01) |
| *E04G 21/12* | (2006.01) |

(52) U.S. Cl.
CPC .............. *B29C 70/541* (2013.01); *B28B 1/14* (2013.01); *B28B 7/303* (2013.01); *B28B 7/306* (2013.01); *E04C 5/076* (2013.01); *E04C 5/122* (2013.01); *E04C 5/125* (2013.01); *E04C 5/163* (2013.01); *E04G 2021/128* (2013.01)

(58) Field of Classification Search
CPC ... E04G 21/12; E04G 2021/128; E04G 15/04; E04C 5/122; E04C 5/12; B28B 7/30; B28B 7/303; B28B 7/306; B28B 1/14; B29C 70/541
See application file for complete search history.

(56) References Cited

U.S. PATENT DOCUMENTS

| | | | | |
|---|---|---|---|---|
| 1,591,907 A | * | 7/1926 | Yager | B28B 7/30 249/17 |
| 3,137,971 A | * | 6/1964 | Rhodes | E04C 5/122 411/455 |
| 3,685,934 A | * | 8/1972 | Huber | E04C 5/122 249/43 |
| 3,766,609 A | * | 10/1973 | Brandestini | E04C 5/122 24/115 R |
| 3,832,438 A | * | 8/1974 | Ditcher | B28B 23/0043 249/145 |
| 3,956,797 A | * | 5/1976 | Brandestini | E04C 5/122 425/111 |
| 4,363,462 A | * | 12/1982 | Wlodkowski | E04C 5/12 24/115 M |

(Continued)

FOREIGN PATENT DOCUMENTS

| | | | | |
|---|---|---|---|---|
| DE | 8108672 U1 | * | 7/1981 | |
| DE | 3123641 A1 | * | 3/1982 | E04C 5/12 |
| JP | 2012202069 A | * | 10/2012 | |

*Primary Examiner* — Adriana Figueroa
*Assistant Examiner* — Jessie T Fonseca
(74) *Attorney, Agent, or Firm* — Adolph Locklar (57) ABSTRACT

A pocket former may include a pocket former body, the pocket former body having an outer surface. The pocket former may further include a collapsible element, the collapsible element formed on the outer surface of the pocket former body. The collapsible element may extend radially outwardly from the pocket former body.

10 Claims, 5 Drawing Sheets

FIG. 1B

(56) References Cited

U.S. PATENT DOCUMENTS

| | | | | |
|---|---|---|---|---|
| 5,072,558 A * | 12/1991 | Sorkin | B29C 45/14 | 52/223.13 |
| 5,271,199 A * | 12/1993 | Northern | E04C 5/12 | 24/122.6 |
| 5,290,006 A * | 3/1994 | Gouker | B28B 7/30 | 249/146 |
| 5,423,362 A * | 6/1995 | Knight | B28B 7/16 | 249/142 |
| 5,749,185 A * | 5/1998 | Sorkin | E04C 5/12 | 24/122.6 |
| 5,755,065 A * | 5/1998 | Sorkin | E04C 5/12 | 52/223.13 |
| 5,788,398 A * | 8/1998 | Sorkin | E04C 5/12 | 285/138.1 |
| 6,023,894 A * | 2/2000 | Sorkin | E04C 5/122 | 24/122.6 |
| 6,027,278 A * | 2/2000 | Sorkin | E04C 5/122 | 403/371 |
| 6,098,356 A * | 8/2000 | Sorkin | E04C 5/12 | 24/122.6 |
| 6,381,912 B1 * | 5/2002 | Sorkin | E04C 5/08 | 24/459 |
| 6,588,193 B2 * | 7/2003 | Hayes | E04C 5/015 | 57/223 |
| 6,631,596 B1 * | 10/2003 | Sorkin | E04C 5/12 | 24/122.6 |
| 6,651,949 B1 * | 11/2003 | Westhoff | B28L 323/00 | 249/142 |
| 6,761,002 B1 * | 7/2004 | Sorkin | E04C 5/12 | 403/374.1 |
| 6,883,280 B2 * | 4/2005 | Hayes | E04C 5/12 | 52/223.13 |
| 7,174,685 B2 * | 2/2007 | Hayes | E04C 5/12 | 52/223.6 |
| 7,275,347 B2 * | 10/2007 | Hayes | E04C 5/12 | 24/122.6 |
| 7,360,342 B2 * | 4/2008 | Hayes | E04C 5/122 | 52/223.13 |
| 7,424,792 B1 * | 9/2008 | Sorkin | E04C 5/122 | 52/223.13 |
| 7,618,217 B2 * | 11/2009 | Henderson | E04H 12/085 | 405/239 |
| 7,621,103 B1 * | 11/2009 | Sorkin | E04C 5/10 | 405/259.1 |
| 7,676,997 B1 * | 3/2010 | Sorkin | E04C 5/12 | 52/223.13 |
| 7,726,082 B2 * | 6/2010 | Hayes | E04C 5/127 | 405/259.1 |
| 7,736,088 B2 * | 6/2010 | Boxall | E01C 11/14 | 249/9 |
| 7,762,029 B2 * | 7/2010 | Hayes | E04C 5/122 | 405/259.1 |
| 7,765,752 B2 * | 8/2010 | Hayes | E04C 5/122 | 403/374.1 |
| 7,793,473 B2 * | 9/2010 | Sorkin | E04C 5/10 | 24/122.6 |
| 7,823,345 B1 * | 11/2010 | Sorkin | E04C 5/122 | 24/122.3 |
| 7,841,061 B1 * | 11/2010 | Sorkin | E04C 5/122 | 24/122.3 |
| 7,856,774 B1 * | 12/2010 | Sorkin | E04C 5/122 | 24/122.6 |
| 7,866,009 B1 * | 1/2011 | Sorkin | F16G 11/048 | 24/136 R |
| D635,278 S * | 3/2011 | Stanford | D25/133 | |
| 7,950,196 B1 * | 5/2011 | Sorkin | E04C 5/10 | 403/314 |
| 7,950,197 B1 * | 5/2011 | Sorkin | E04C 5/10 | 403/314 |
| 7,963,078 B1 * | 6/2011 | Sorkin | E04C 5/122 | 24/122.3 |
| 8,015,774 B1 * | 9/2011 | Sorkin | E04C 5/122 | 403/368 |
| 8,051,615 B2 * | 11/2011 | Mathews | F16G 11/106 | 403/78 |
| 8,065,845 B1 * | 11/2011 | Sorkin | E04C 5/122 | 24/115 M |
| 8,069,624 B1 * | 12/2011 | Sorkin | E04C 5/12 | 403/314 |
| 8,087,204 B1 * | 1/2012 | Sorkin | E04C 5/122 | 52/223.13 |
| 8,251,344 B1 * | 8/2012 | Sorkin | E04C 5/122 | 249/177 |
| 8,286,309 B2 * | 10/2012 | Landry | F16G 11/048 | 24/122.6 |
| 8,756,885 B1 * | 6/2014 | Mathews | E04C 5/122 | 403/369 |
| 8,904,721 B2 * | 12/2014 | Pantelides | E01D 19/16 | 52/223.1 |
| 8,925,279 B2 * | 1/2015 | Pantelides | E01D 19/16 | 52/223.1 |
| 8,931,152 B2 * | 1/2015 | Parente | B25B 27/00 | 29/253 |
| 9,096,986 B2 * | 8/2015 | Henderson | E04C 5/125 | |
| 9,097,014 B1 * | 8/2015 | Sorkin | E04C 5/122 | |
| 9,163,405 B2 * | 10/2015 | Mathews | E04C 5/122 | |
| 9,303,406 B2 * | 4/2016 | Sorkin | E04L 31/16 | |
| 9,317,191 B2 * | 4/2016 | Stanford | E04C 5/122 | |
| 9,399,869 B2 * | 7/2016 | Sorkin | E04C 5/12 | |
| 2002/0007604 A1 * | 1/2002 | Wallstein | E04C 5/122 | 52/223.13 |
| 2002/0096619 A1 * | 7/2002 | Lancelot, III | B28B 23/005 | 249/91 |
| 2004/0111992 A1 * | 6/2004 | Bennett | B28B 7/30 | 52/380 |
| 2006/0033003 A1 * | 2/2006 | Watson | B28B 7/28 | 249/177 |
| 2006/0179742 A1 * | 8/2006 | Mathews | E04C 5/122 | 52/223.13 |
| 2006/0201083 A1 * | 9/2006 | Hayes | E04C 5/12 | 52/223.13 |
| 2007/0289239 A1 * | 12/2007 | Lee | E02D 31/02 | 52/426 |
| 2008/0083130 A1 * | 4/2008 | Parkes | E01C 11/14 | 33/562 |
| 2012/0011788 A1 * | 1/2012 | Nieto | E04C 5/122 | 52/223.13 |
| 2013/0037979 A1 * | 2/2013 | Hanson | E04C 3/34 | 264/35 |
| 2014/0083031 A1 * | 3/2014 | Dunlop | E04C 5/16 | 52/223.14 |
| 2015/0300021 A1 * | 10/2015 | Hayes | B28B 23/046 | 33/700 |
| 2015/0330078 A1 * | 11/2015 | Sorkin | E04B 1/66 | 52/223.13 |
| 2015/0336289 A1 * | 11/2015 | Comerford | E04G 15/04 | 264/317 |
| 2016/0208490 A1 * | 7/2016 | Wilson | E04C 5/08 | |

* cited by examiner

COLLAPSIBLE ELEMENT POCKET FORMER

CROSS-REFERENCE TO RELATED APPLICATIONS

This application is a divisional application which claims priority from U.S. utility application Ser. No. 15/226,487, filed Aug. 2, 2016 which is itself a nonprovisional application that claims priority from U.S. provisional application No. 62/200,966, filed Aug. 4, 2015, which is hereby incorporated by reference in its entirety.

TECHNICAL FIELD/FIELD OF THE DISCLOSURE

The present disclosure relates generally to post-tensioned, prestressed concrete construction. The present disclosure relates specifically to methods and apparatuses for forming a pocket in a post-tensioned, prestressed concrete member.

BACKGROUND OF THE DISCLOSURE

Many structures are built using concrete, including, for instance, buildings, parking structures, apartments, condominiums, hotels, mixed-use structures, casinos, hospitals, medical buildings, government buildings, research/academic institutions, industrial buildings, malls, roads, bridges, pavement, tanks, reservoirs, silos, sports courts, and other structures.

Prestressed concrete is structural concrete in which internal stresses are introduced to reduce potential tensile stresses in the concrete resulting from applied loads; prestressing may be accomplished by post-tensioned prestressing or pre-tensioned prestressing. In post-tensioned prestressing, a tension member is tensioned after the concrete has attained a desired strength by use of a post-tensioning tendon. The post-tensioning tendon may include for example and without limitation, anchor assemblies, the tension member, and sheathes. Traditionally, a tension member is constructed of a material that can be elongated and may be a single or a multi-strand cable. Typically, the tension member may be formed from a metal or composite material, such as reinforced steel. The post-tensioning tendon conventionally includes an anchor assembly at each end. The post-tensioning tendon is fixedly coupled to a fixed anchor assembly positioned at one end of the post-tensioning tendon, the "fixed-end", and stressed at the stressed anchor assembly positioned at the opposite end of the post-tensioning tendon, the "stressing-end" of the post-tensioning tendon.

A pocket former may be used to prevent or restrict concrete from filling in the area between the stressing-end anchor and the concrete form used to form the concrete member to allow access to the stressing-end of the tendon once the concrete member is poured. As understood in the art, the concrete form is a form or mold into which concrete is poured or otherwise introduced to give shape to the concrete member as it sets or hardens, thus forming the concrete member. Once the concrete has sufficiently hardened and the concrete form is removed, the pocket former is removed from the concrete member. In certain conventional uses, pocket formers are frustoconical in shape to facilitate removal from the concrete member. Conventionally, once the tendon is stressed, the pocket formed by the pocket former is filled with a material such as a cementitious grout or concrete to, for example, provide fire protection and corrosion protection.

SUMMARY

The present disclosure provides for a pocket former. The pocket former includes a pocket former body, the pocket former body having an outer surface. The pocket former further includes a collapsible element, the collapsible element formed on the outer surface of the pocket former body. The collapsible element extends radially outwardly from the pocket former body.

The disclosure also provides for a pocket former. The pocket former includes a pocket former body, the pocket former body having an outer surface. The pocket former body has an inner portion and an outer portion. The pocket former also includes a collapsible element, the collapsible element flexibly coupled to the inner portion and the outer portion of the pocket former body.

The disclosure additionally provides for a pocket former. The pocket former includes a pocket former body, the pocket former body having an outer surface. The pocket former also includes a collapsible element, the collapsible element pivotably coupled to the pocket former body.

The present disclosure also provides for a method of forming a post-tensioned concrete member. The method includes positioning a post-tensioning tendon within a concrete form, the post-tensioning tendon including a tension member, fixed anchor, and a stressing end anchor. The method also includes positioning a pocket former between the stressing end anchor and the concrete form. The pocket former includes a pocket former body, the pocket former body having an outer surface. The pocket former body has a tension member channel therethrough. The pocket former also includes a collapsible element, the collapsible element formed on the outer surface of the pocket former body. The collapsible element extends radially outwardly from the pocket former body. The method additionally includes inserting the tension member through the tension member channel of the pocket former body and placing concrete into the concrete form such that the post-tensioning tendon and the pocket former are encased in the concrete. The method includes applying force to the pocket former body and collapsing the collapsible element into the pocket former body. The method also includes forming a cavity within the concrete by removing the pocket former body from the concrete.

BRIEF DESCRIPTION OF THE DRAWINGS

The present disclosure is best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

DETAILED DESCRIPTION

It is to be understood that the following disclosure provides many different embodiments, or examples, for implementing different features of various embodiments. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed.

Figure 1A:
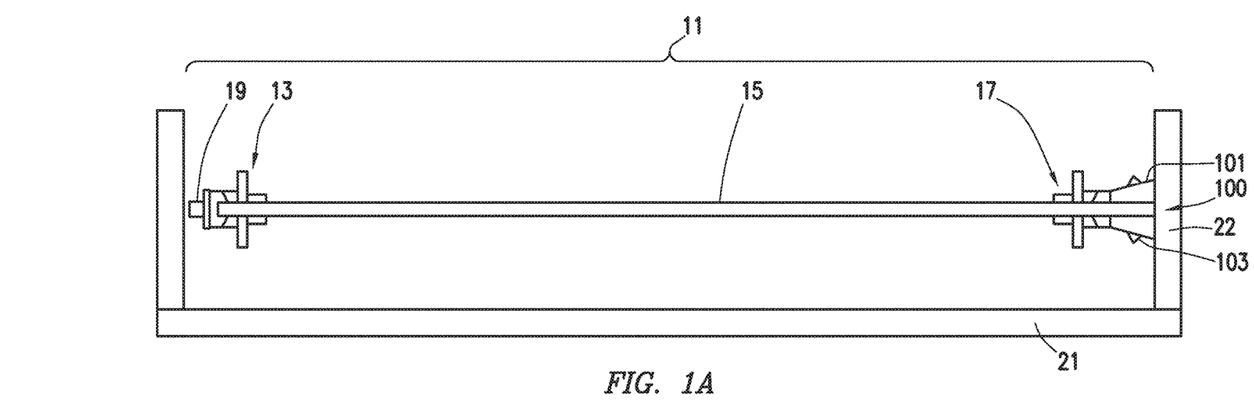
FIGS. 1A, 1B depict a partial cross section of a post-tensioning tendon within a concrete form during stages of a concrete pouring procedure consistent with embodiments of the present disclosure.
Figure 1B:
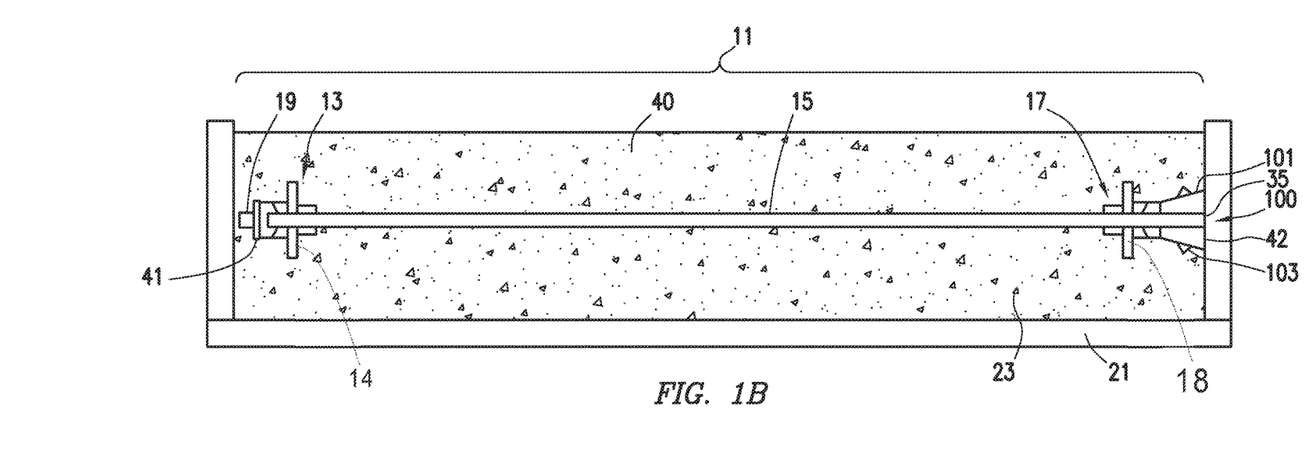

When stressing concrete member 40, anchoring systems may be provided to hold the tension member before and after stressing. In some embodiments, as depicted in FIGS. 1A, 1B, post-tensioning tendon 11 may be positioned within concrete form 21. Concrete form 21 is a form into which concrete may be poured to form concrete member 40. Post-tensioning tendon 11 may include for example and without limitation fixed end anchor 13, tension member 15, and stressing end anchor 17. In some embodiments, post-tensioning tendon 11 may also include a sheath positioned about tension member 15 and one or more seals between the sheath and fixed end anchor 13, stressing end anchor 17. The sheath and seals may, for example, protect tension member 15 from corrosion after concrete 23 (shown in FIG. 1B) is poured. Additionally, the sheath and seals may, for example, prevent or retard concrete from ingressing into tension member 15 and preventing or retarding the tensioning of tension member 15. In some embodiments, a seal for fixed end anchor 13 may be omitted. Fixed-end anchor body 14 may be positioned within concrete form 21 such that fixed-end anchor 13 will be encased in concrete 23 after concrete is poured into concrete form 21. In some embodiments, fixed end cap 19 may be positioned at distal end 41 of fixed end anchor 13. Fixed end cap 19 may, in certain embodiments, protect tension member 15 from corrosion after concrete 23 is poured by preventing or retarding corrosive or reactive fluids or concrete from contacting tension member 15.

Pocket former 100 may be positioned between stressing end anchor body 18 and end wall 22 of concrete form 21. Pocket former 100 may prevent or restrict concrete 23 from filling the space between stressing end anchor 17 and end wall 22, thus forming a cavity or pocket in edge 42 of concrete member 40 formed by concrete 23 within concrete form 21. Pocket former 100 may thus allow access to tension member 15 from outside concrete member 40 once concrete member 40 is sufficiently hardened and end wall 22 is removed.

Figure 1C:
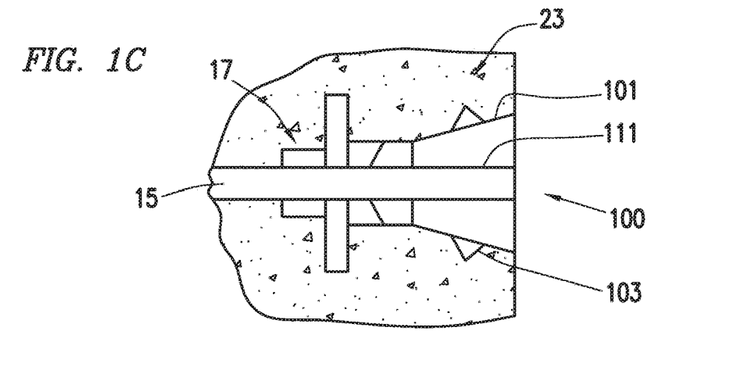
FIGS. 1C-1E depict an anchor consistent during stages of a concrete pouring procedure consistent with embodiments of the present disclosure.
Figure 1D:
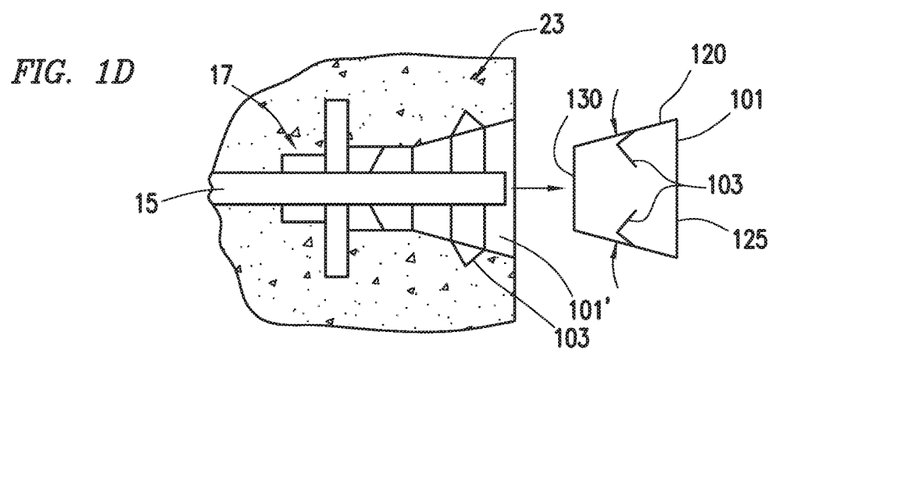
Figure 1E:
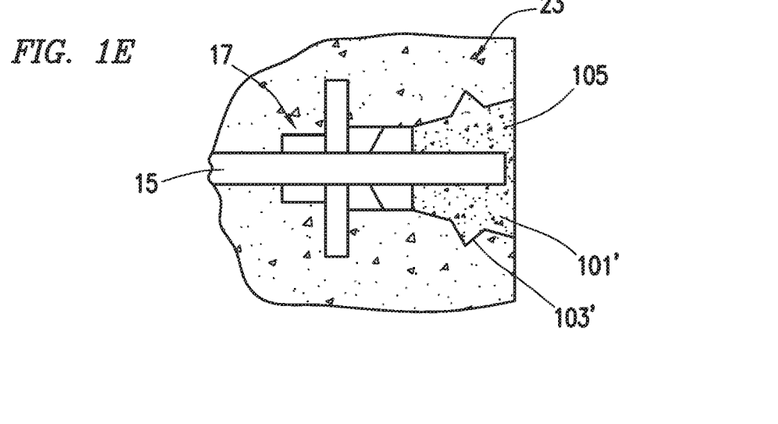

In some embodiments, as depicted in FIG. 1C, pocket former 100 may include pocket former body 101. In some embodiments, pocket former body 101 may include a coupler for coupling pocket former 100 to stressing end anchor 17. In some embodiments, pocket former body 101 may be hollow. In some embodiments, pocket former body 101 may include tension member channel 111 through which tension member 15 may pass when pocket former 100 is installed onto stressing end anchor 17. In some embodiments, pocket former body 101 may be a cylindrical or generally cylindrical member. Pocket former body 101 may be any shape suitable for providing a pocket in concrete 23 to allow access to the end of tension member 15 including, but not limited to, cylindrical, frustoconical, prismatoidal, ellipsoidal, or any combination thereof. Additionally, the cross-sectional shape of pocket former body 101 may be any shape including, but not limited to, square, round, oblong, ovate, ellipsoidal, triangular, polyhedral, or any combination thereof. As depicted in FIGS. 1C-E, pocket former body 101 may be frustoconical or otherwise tapered from pocket former outer edge 125 to pocket former inner edge 130. In some embodiments, by tapering pocket former body 101 from pocket former outer edge 125 to pocket former inner edge 130, removal of pocket former body 101 from concrete 23 may be accomplished more easily than a non-tapered pocket former body. As depicted in FIG. 1D, when pocket former body 101 is removed from concrete 23 (once concrete 23 has reached a sufficient strength), cavity 101' is formed in concrete 23. The shape of cavity 101' may correspond with the outside shape of pocket former body 101.

In some embodiments, pocket former 100 may further include one or more collapsible elements 103. "Collapsible element," as used herein, refers to an attachment to or integrally formed part of pocket former body 101 that collapses inward towards a pocket former body 101, such as shown in FIG. 1D, or pocket former interior, such as pocket former interior 230, as shown in FIG. 2B, when placed under compressive force. Collapsible elements may be formed from such materials as plastic or metal. Non-limiting examples of collapsible elements are described hereinbelow.

As depicted in FIGS. 1C-E, in some embodiments, collapsible element 103 may be formed on outer surface 120 of pocket former body 101. As depicted in FIGS. 1C-E, collapsible element 103 may extend radially outwardly from pocket former body 101. As depicted in FIG. 1D, when pocket former 100 is removed from concrete 23, collapsible element 103 may collapse, compress, or otherwise deform towards pocket former body 101, allowing pocket former 100 to be removed from concrete 23. After removal of pocket former 100, keyway 103' may be formed in concrete 23 corresponding with the outside shape of pocket former body 101 and collapsible element 103. As shown in FIG. 1D, keyway 103' is a cavity within concrete 23.

With further direction to FIGS. 1C-E, in some embodiments, once pocket former body 101 and collapsible element 103 are removed from concrete 23, tension member 15 may be placed under tensile stress. In some embodiments, stressing end anchor 17 may allow tension member 15 to extend and be stressed against fixed end anchor 13, while preventing or restricting retraction of tension member 15 once tension member 15 is stressed. In some embodiments, tension member 15 may be cut to length such that tension member 15 does not, for example, extend beyond edge 42 of concrete 23. In some embodiments, once tension has been applied to tension member 15, cavity 101' and keyway 103' may, as depicted in FIG. 1E, be filled with filling material 105. Filling material 105 may be grout, a cementitious chloride-free grout, or concrete. In some embodiments, a stressed end cap may be installed over end 35 of tension member 15 to prevent or restrict filling material 105 from entering stressing end anchor 17 and tension member 15. In some embodiments, keyway 103' may provide more surface area than in concrete 23 without keyway 103' and/or one or more locking features into which filling material 105 may be placed, thus preventing or restricting filling material 105 from delaminating or otherwise detaching from or moving relative to concrete 23. In some embodiments, locking features may include, for example and without limitation, textured surfaces, ridges, grooves, recesses, or protrusions from or into concrete 23 adapted to prevent movement of filling material 105 relative to concrete 23. Such locking features may be formed, for example and without limitation, by textured surfaces, ridges, grooves, recesses, or protrusions formed on outer surface 120 of pocket former body 101.

FIGS. 1A-E depict embodiments in which collapsible element 103 is at least partially annular and triangular in cross section, thus forming keyway 103' that is generally annular and triangular.

In some embodiments, pocket former body 101 may be formed from a rigid material capable of retaining its shape when concrete 23 is poured. In some embodiments, collapsible element 103 may be formed from an elastic or pliable material that may allow collapsible element 103 to deform, thus allowing easier removal from concrete 23 than if collapsible element 103 were rigid. In some embodiments, collapsible element 103 may be formed from multiple subcomponents. In some such embodiments, portions of collapsible element 103 may be formed from a rigid material, while other portions are formed from a more pliable material.

Figure 2A:
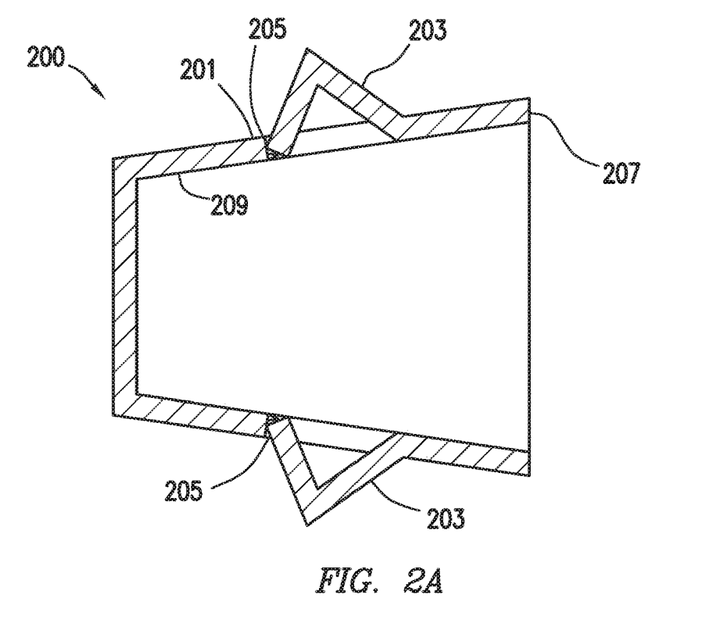
FIGS. 2A, 2B depict a pocket former consistent with embodiments of the present disclosure.
Figure 2B:
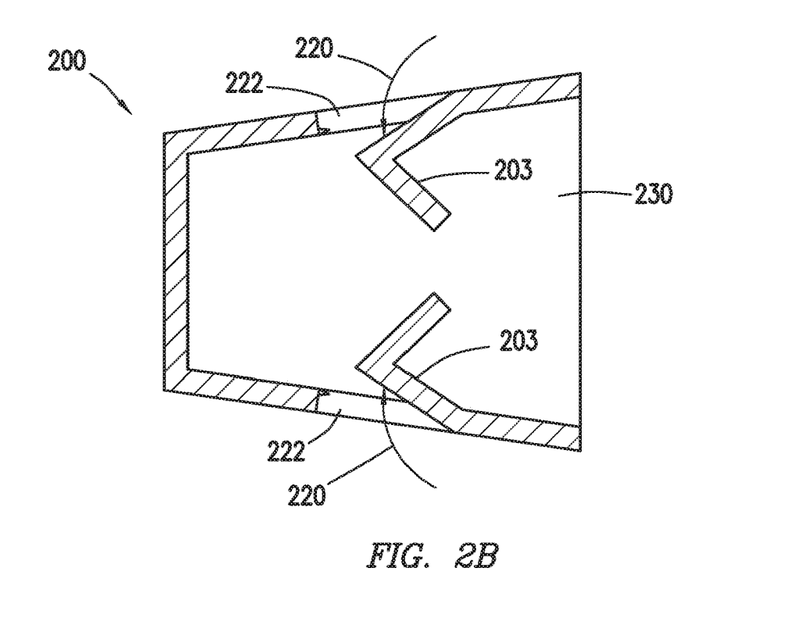

In some embodiments, as depicted in FIGS. 2A, 2B, pocket former 200 may include collapsible elements 203 and pocket former body 201. Pocket former body 201 may include pocket former first portion 207 and pocket former second portion 209. Collapsible elements 203 may couple between pocket former first portion 207 and pocket former second portion 209. In some embodiments, pocket former 200 may be formed by injection molding. In some embodiments, collapsible element 203 may be flexibly coupled to pocket former body 201 such that upon removal from concrete 23, collapsible elements 203 may collapse, compress, or otherwise deform inward to form collapsible element keyway 222 formed along lines 220 as depicted in FIG. 2B. As further shown in FIG. 2B, upon application of compressive force, collapsible elements 203 detach from pocket former second portion 209. In some embodiments, collapsible pocket former 200 may further include pocket former bridge 205. Pocket former bridge 205 may couple pocket former second portion 209 to collapsible elements 203. Pocket former bridge 205 may be less thick than the pocket former second portion 209, allowing pocket former bridge 205 to decouple from pocket former second portion 209 when pocket former 200 is removed from concrete 23. In other embodiments, pocket former bridge 205 may include cut or slit formed in pocket former body 201. Pocket former bridge 205 may seal against infiltration of concrete 23 into the interior of pocket former 200 while providing a structurally weakened area to allow, for example and without limitation, separation between collapsible elements 203 and pocket former second portion 209. As depicted in FIGS. 2A, 2B, in some embodiments, pocket former bridge 205 may be formed about at least a portion of the perimeter of collapsible elements 203 and may serve to allow collapsible elements 203 to, as depicted in FIG. 2B, collapse into the interior of pocket former 200.

Figure 3A:
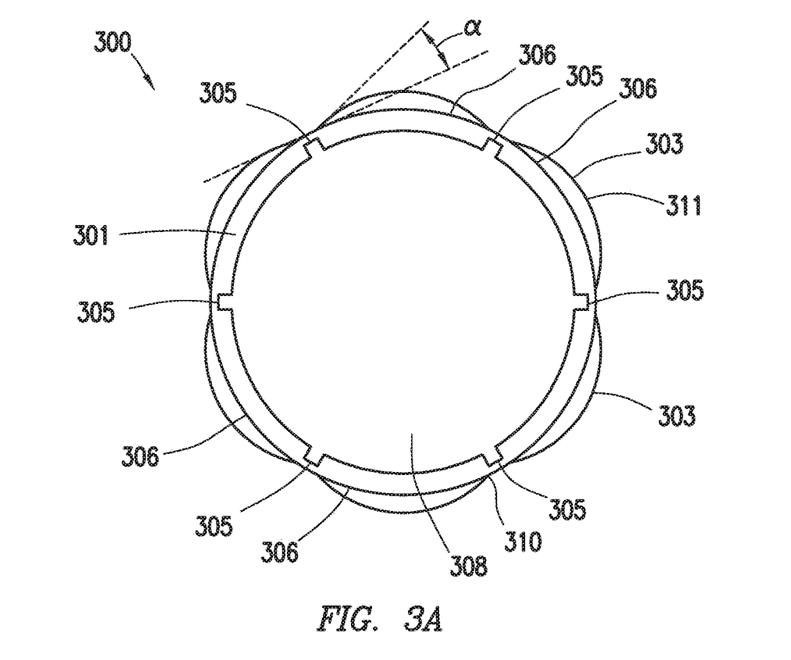
FIGS. 3A, 3B depict a pocket former consistent with embodiments of the present disclosure.
Figure 3B:
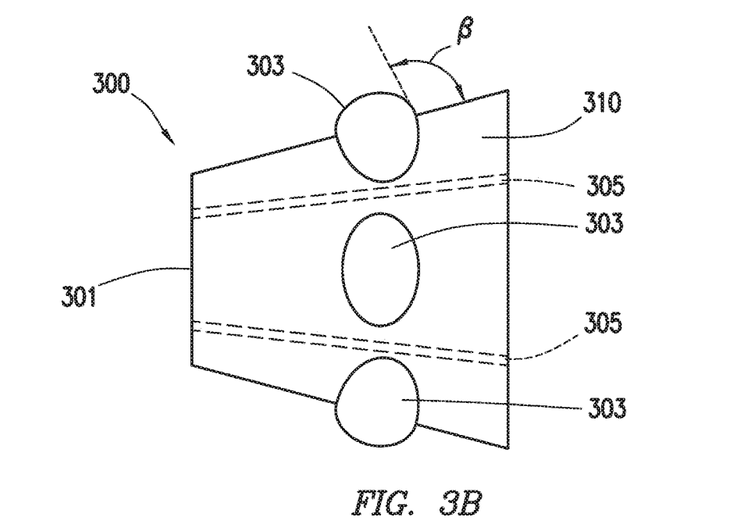

In some embodiments, as depicted in FIGS. 3A, 3B, pocket former 300 may include collapsible elements 303 positioned about and attached to pocket former body 301. In some embodiments, pocket former 300 may include pocket former bridges 305. Pocket former bridges 305 are oriented longitudinally along pocket former body 301 such that, when sufficient force is applied to pocket former bridges 305, pocket former bridges 305 may break and pocket former body 301 may separate into two or more longitudinal segments 306. Longitudinal segments 306 that are attached to collapsible elements 303 may then flex into the pocket former interior 308 of pocket former 300, allowing removal of pocket former 300 from concrete 23. Although depicted as symmetrically arranged about pocket former body 301, pocket former bridges 305 may be positioned in any configuration without deviating from the scope of this disclosure.

In some embodiments, as depicted in FIGS. 3A, 3B, collapsible elements 303 may extend radially outward from outer surface 310 of pocket former body 301. In some embodiments, the collapsible elements outer surface 311 may have a curved profile. In some such embodiments, cross-sectional angle $\alpha$ of collapsible elements 303 may be smaller than longitudinal angle $\beta$. In some such embodiments, because cross-sectional angle $\alpha$ is smaller than longitudinal angle $\beta$, the retraction of collapsible elements 303 of pocket former 300 may be achieved by the rotation of pocket former 300. Because cross-sectional angle $\alpha$ is smaller than longitudinal angle $\beta$, collapsible elements 303 may allow pocket former 300 to rotate within concrete 23, while adding inward pressure on collapsible elements 303, pushing collapsible elements 303 into pocket former body 301. This inward force may cause the breakage of pocket former bridges 305. Although described as longitudinal, pocket former bridges 305 may be of any geometry and pocket former bridges 305 may be utilized with curved collapsible elements 303 without deviating from the scope of this disclosure.

Figure 4:
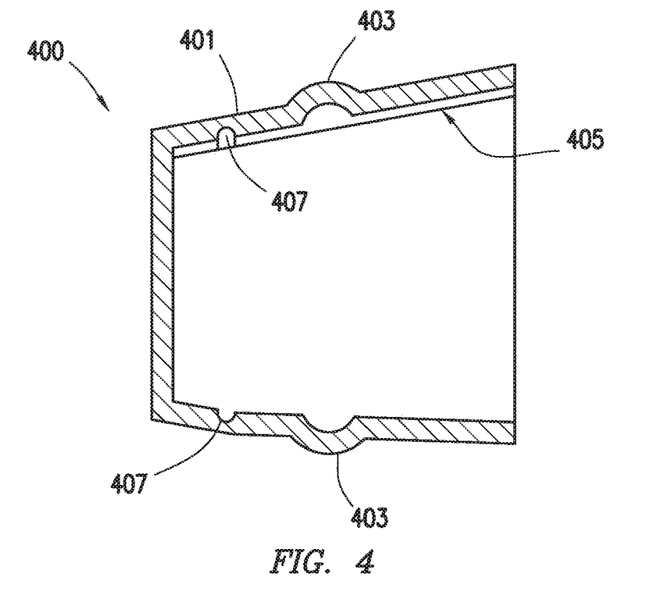
FIG. 4 depicts a cross section of a pocket former consistent with embodiments of the present disclosure.

In some embodiments, as depicted in FIG. 4, pocket former 400 may include pocket former body 401 and collapsible element 403. Pocket former body 401 may also include flex feature 407 that allows flexure between collapsible element 403 and pocket former body 401. Flex feature 407 may, for example and without limitation, be a thinner portion of pocket former body 401 than the remainder of pocket former body 401, different material of pocket former body 401 than the rest of pocket former body 401, a hinge, a connection or a coupling, and may allow collapsible element 403 to bend inward without separating from pocket former body 401.

In some embodiments, collapsible elements 403 may be formed from a different material than the rest of pocket former body 401. In some embodiments, collapsible elements 403 may be formed together with pocket former body 401 by, for example and without limitation, injection molding, using a different material in the portions of the mold corresponding to the collapsible elements 403 than the rest of pocket former body 401. In some embodiments, collapsible elements 403 may be formed separately from pocket former body 401 and may be coupled thereto. In some embodiments, pocket former body 401 may be formed from a flexible material. In some embodiments, collapsible elements 403 may be formed from a rigid material, thus, for example and without limitation, retaining the shape of collapsible elements 403 while allowing pocket former body 401 to flex when removed from concrete 23. In some embodiments, pocket former body 401 may be formed from a rigid material and collapsible elements 403 may be formed from a flexible material. In some embodiments, a portion of pocket former body 401, such as pocket former bridge 405 or flex fixture 407 may be formed from a flexible material with pocket former body 401 and collapsible elements 403 formed from a rigid material.

Figure 5:
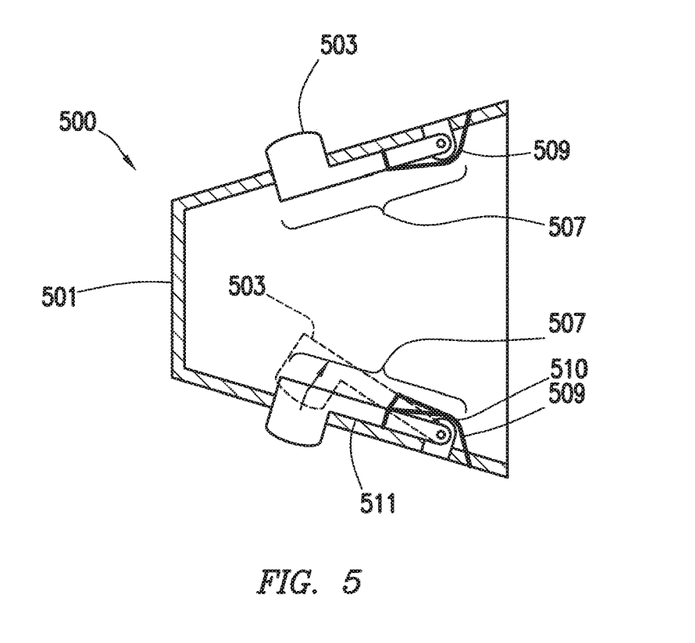
FIG. 5 depicts a cross section of a pocket former consistent with embodiments of the present disclosure.

In some embodiments, as depicted in FIG. 5, collapsible elements 503 of pocket former 500 may be springedly coupled to pocket former body 501 by spring mechanism 507. In some such embodiments, spring mechanism 507 may include connecting member 511 mechanically attached or formed integrally with pivot 510 and spring 509. Spring 509 may connect pivot 510 to pocket former body 501. Spring mechanism 507 may allow collapsible elements 503 to move radially inward without breakage of pocket former 500. In some such embodiments, collapsible elements 503 may be biased into the outward position by spring 509. When removed from concrete 23, collapsible elements 503 may collapse inward into pocket former body 501. Once pocket former 500 is removed from concrete 23, spring 509 may return collapsible elements 503 to the outward position, allowing pocket former 500 to be reused.

The foregoing outlines features of several embodiments so that a person of ordinary skill in the art may better understand the aspects of the present disclosure. Such features may be replaced by any one of numerous equivalent alternatives, only some of which are disclosed herein. One of ordinary skill in the art should appreciate that they may readily use the present disclosure as a basis for designing or modifying other processes and structures for carrying out the same purposes and/or achieving the same advantages of the embodiments introduced herein. One of ordinary skill in the art should also realize that such equivalent constructions do not depart from the spirit and scope of the present disclosure and that they may make various changes, substitutions and alterations herein without departing from the spirit and scope of the present disclosure. Nothing herein is a definition of any word or term as generally used by a person of ordinary skill in the art, and nothing herein is a disavowal of any scope of any word or term as generally used by a person of ordinary skill in the art.

The invention claimed is:

1. A pocket former comprising:
   a pocket former body, the pocket former body having an outer surface and including at least one pocket former bridge oriented longitudinally along the pocket former body; and
   a collapsible element, the collapsible element formed on the outer surface of the pocket former body, the collapsible element extending radially outwardly from the pocket former body;
   wherein the at least one pocket former bridge is less thick than the rest of the pocket former body so that upon the application of a force on the collapsible element, the at least one pocket former bridge breaks such that the pocket former body separates into two or more segments.

2. The pocket former of claim 1, wherein the pocket former body is tapered from a pocket former outer edge to a pocket former inner edge.

3. The pocket former of claim 1, wherein the outer surface of the pocket former body includes textured surfaces, ridges, grooves, recesses, or protrusions.

4. The pocket former of claim 1, wherein the collapsible element has an exterior surface and wherein the exterior surface of the collapsible element has a curved profile.

5. The pocket former of claim 4, wherein the collapsible element has a cross-sectional angle $\alpha$ and a longitudinal angle $\beta$, and wherein the cross-sectional angle $\alpha$ is smaller than the longitudinal angle $\beta$.

6. The pocket former of claim 1, wherein the pocket former body further comprises a flex feature.

7. The pocket former of claim 1 wherein upon the application of a force on the collapsible element, the at least one pocket former bridge breaks such that the pocket former body separates into two or more longitudinal segments.

8. A pocket former comprising:
   a pocket former body, the pocket former body having an outer surface, the pocket former body having a first portion and a second portion and including at least one pocket former bridge oriented longitudinally along the pocket former body; and
   a collapsible element, the collapsible element flexibly coupled to the first portion and the second portion of the pocket former body;
   wherein the at least one pocket former bridge is less thick than the rest of the pocket former body so that upon the application of a force on the collapsible element, the at least one pocket former bridge breaks such that the pocket former body separates into two or more segments.

9. The pocket former of claim 8 wherein upon the application of a force on the collapsible element, the at least one pocket former bridge breaks such that the pocket former body separates into two or more longitudinal segments.

10. A pocket former comprising:
    a pocket former body;
    a collapsible element; and
    a spring mechanism, the spring mechanism mechanically connected to the collapsible element and the pocket former body, wherein the spring mechanism comprises:
    a connecting member, the connecting member mechanically attached or formed integrally with a pivot and wherein the connecting member mechanically connects to the collapsible element; and
    a spring, wherein the spring connects the pivot to the pocket former body.

\* \* \* \* \*